(12) United States Patent
Richmond et al.

(10) Patent No.: US 6,345,202 B2
(45) Date of Patent: Feb. 5, 2002

(54) METHOD OF TREATING OBSTRUCTIVE SLEEP APNEA USING IMPLANTABLE ELECTRODES

(75) Inventors: Frances J. R. Richmond; Gerald E. Loeb, both of South Pasadena, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/812,447

(22) Filed: Mar. 20, 2001

Related U.S. Application Data

(62) Division of application No. 09/370,082, filed on Aug. 6, 1999, now Pat. No. 6,240,316.
(60) Provisional application No. 60/096,495, filed on Aug. 14, 1998, and provisional application No. 60/118,840, filed on Feb. 5, 1999.

(51) Int. Cl.[7] .................................................. A61N 1/36
(52) U.S. Cl. ........................................................ 607/42
(58) Field of Search .............................. 607/42, 48, 72, 607/118, 2; 128/898

(56) References Cited

U.S. PATENT DOCUMENTS

| | | | | |
|---|---|---|---|---|
| 5,549,655 A | * | 8/1996 | Erickson | |
| 5,591,216 A | * | 1/1997 | Testerman et al. | |
| 5,792,067 A | * | 8/1998 | Karell | |
| 6,132,384 A | * | 10/2000 | Christopherson et al. | |
| 6,198,970 B1 | * | 3/2001 | Freed et al. | |
| 6,240,316 B1 | * | 5/2001 | Richmond et al. | |
| 6,269,269 B1 | * | 7/2001 | Ottenhoff et al. | |

* cited by examiner

Primary Examiner—Jeffrey R. Jastrzab
(74) Attorney, Agent, or Firm—Bryant R. Gold; Laura Haburay Bishop

(57) ABSTRACT

Electrodes are implanted at strategic locations within a patient and are then controlled in a manner so as to stimulate muscle and nerve tissue in a constructive manner which helps open blocked airways. In a preferred method, at least one microstimulator treats sleep apnea in an open loop fashion by providing electrical stimulation pulses in a rhythm or cycle having a period corresponding approximately to the natural respiratory rhythm of the patient. Such open loop stimulation entrains the patient's respiratory rate to follow the pattern set by the microstimulator so that stimulation is applied to open the airway during a period of inspiration by the patient.

8 Claims, 4 Drawing Sheets

METHOD OF TREATING OBSTRUCTIVE SLEEP APNEA USING IMPLANTABLE ELECTRODES

This application is a divisional application of U.S. application Ser. No. 09/370,082, filed Aug. 6, 1999, which application, including its Appendix A filed therewith, is incorporated herein by reference. Now U.S. Pat. No. 6,240, 316 which claims benefit of Prov. No. 60/096,495 filed Aug. 14, 1998, and 60/118,840 filed Feb. 5, 1999.

BACKGROUND OF THE INVENTION

The present invention relates to a system and method for treating sleep apnea, and more particularly to a system and method for treatment of obstructive sleep apnea using implantable microstimulators.

Sleep apnea is the inability to breath while sleeping. The most common cause is a mechanical obstruction of the airway. This can arise from a variety of causes acting at a variety of sites, as described in detail by the report of Dr. Frances J. R. Richmond (attached as Appendix A to the parent application, Ser. No. 09/370,082). At each of these sites, various muscles are available whose mechanical action can be used to open the airway. Thus, in principle, it should be possible to stimulate these muscles electrically at appropriate times during sleep to produce contractions that maintain patency or open an obstructed airway. It may also be possible to produce muscle contractions via reflexes. Sensory axons that are present in the muscle nerves or in separate nerves supplying skin or mucous membranes may have connections in the spinal cord or brain stem to the motor neurons that control these muscles. Electrical stimulation of these sensory axons would then result in the desired muscle contractions.

Unfortunately, the muscles that control the airway and the nerves that supply them are, for the most part, located deep in the neck and oropharynx, adjacent to many vital and delicate structures. The present invention describes an approach in which very small electronic devices can be implanted with minimal surgical intervention in order to control these muscles to prevent or interrupt sleep apnea without disturbing the sleeping patient.

Obstructive sleep apnea (OSA) is characterized by frequent periods of airway occlusion during sleep, with concomitant obstruction of inspiratory airflow, drop in blood oxygen and interruption of sleep when the patient awakes to use voluntary muscle contraction to open the airway and take a few deep breaths. The mechanical locations and structural causes of obstruction are multiple. The most frequent mechanisms include settling of the tongue, uvula, soft palate or other tissues against the airway during the negative pressure associated with inspiration. This may be related to adipose tissue accumulation, lack of muscle tone or inadequate central respiratory drive to the tongue and/or other accessory respiratory muscles around the oropharyngeal airway.

Current treatments for OSA include behavioral control of sleep posture (e.g. sewing a tennis ball in the back of a pajama shirt), positive airway pressure applied via a face mask and ventilating pump, and surgical reduction of the soft tissues in the airway. Disadvantageously, patient compliance with noninvasive methods is low. Clinical success rates with surgery are mixed because the exact mechanical problem is often unclear, the extent of the surgery is limited for practical reasons, and the soft tissue may regrow.

Recently, a fully implanted system using functional electrical stimulation has been developed in a collaboration between Johns Hopkins University and Medtronic Corp. It includes an implanted pressure sensor, electronic controller and a nerve cuff electrode on the genioglossal nerve, which is used to stimulate the motor axons that control tongue protrusion. The onset of each inspiratory phase is detected by sensing the negative pressure wave under the manubrium of the sternum, which triggers a preset train of stimuli that causes the tongue muscles to contract, lifting it away from the posterior oropharynx to prevent occlusion from occurring. In a small clinical trial, this system had some success, but it is highly invasive and prone to complications from the surgical placement of the sensor and nerve cuff. Furthermore, the algorithm for detecting the onset of inspiration is complex and prone to error as a result of mechanical artefacts from cardiac pulsation and postural movements.

Electrical stimulation of muscles with intact motor supply, such as in OSA patients, typically involves activation of the large diameter axons of the motor neurons that, in turn, activate the muscle fibers to contract. Electrical stimulation may be achieved by several routes. Transcutaneous electrical and magnetic stimulation are noninvasive but relatively nonselective, usually producing substantial activation of cutaneous sensory nerves that results in intrusive and often disagreeable sensations. Nerve trunk stimulation via surgically implanted nerve cuff or epineural electrodes stimulates both the motor and sensory axons that run in those nerves. The largest diameter fibers of both types tend to be excited first and there is little conscious sensation associated with the large diameter proprioceptive fibers in muscle, as opposed to cutaneous, nerves. However, it is thus difficult to achieve reliable stimulation of only the largest fibers because the recruitment curves are relatively steep. Muscle nerves do contain smaller diameter sensory fibers that signal pain, pressure and other undesirable sensations. Furthermore, many muscle nerves supply axons to multiple muscles or compartments of muscles that may have different and perhaps undesirable actions. For example, the more proximal and surgically accessible portion of the genioglossal nerve supplies portions of the tongue muscles that actually retract rather than protrude the tongue. Intramuscular wires tend to recruit motor and proprioceptive axons in only the compartment of muscle in which they are located, but they are difficult to implant and maintain without migration or breakage as a result of the constant motion of the muscle and the traction of attached leads. It is thus seen that there is a need for a better vehicle for treating obstructive sleep apnea than has heretofore been available.

Respiration can be viewed as an oscillator whose frequency is determined by several different neural and mechanical control loops involving metabolic rate, neural sensing of oxygen and carbon dioxide levels in the blood stream, respiratory muscle activity, airway impedance and tidal volume. Individuals with normal airways tend to have fairly regular respiratory rhythms punctuated by occasional irregularities such as deep sighs that help to clear poorly ventilated portions of the lung and keep alveoli inflated. Conscious and semiconscious individuals can be ventilated artificially by a respirator that applies positive pressure to force air into the lungs at a regular interval, but it is often difficult to match the ventilation so applied to the perceived need for air by the patient and his/her nervous system, which may result in the patient "fighting" the ventilator. Nevertheless, biological oscillators are easily entrained to periodic external events as long as the frequency of those events is sufficiently close to the natural period of the biological oscillator. This is a general property of systems of loosely coupled oscillators, as originally described mathematically by Arthur T. Winfree (*The Geometry of Biological Time,* Springer Study Edition, 1991) and may also reflect plastic properties of the nervous system that underlie learning and adaptive control for many sensorimotor behaviors.

SUMMARY OF THE INVENTION

In contrast to all of the above approaches for treating obstructive sleep apnea, or OSA, the present invention teaches the use of microminiature, leadless stimulators called Bionic Neurons, or BION™ stimulators, or "microstimulators", that receive power signals (and/or, in some embodiments, recharging signals) and control signals by inductive or RF coupling to a radio frequency magnetic field generated outside the body. Such "microstimulators" are implanted at strategic locations within the patient and controlled in a manner so as to stimulate muscle and nerve tissue in a constructive manner to help open blocked airways. Thus, it is seen that a key aspect of the present invention is that obstructive sleep apnea is treated by electrically stimulating certain muscles of the oropharynx using one or more microstimulators in order to contract and thereby pull open the obstructed airway.

It should be noted that the present invention is not directed to the "microstimulator", per se, which is the subject of other patents and patent applications, but is rather directed to a method of using the microstimulator, or a group of microstimulators, to treat sleep apnea.

As indicated, the invention teaches the treatment of sleep apnea by electrical stimulation of nerves and muscles by means of one or more microstimulators located at the site(s) of stimulation. Advantageously, one or more such devices may be easily implanted into the desired locations in the body using minimally invasive, outpatient procedures under local anesthesia. Additionally, such devices receive power and programming (control) signals by inductive or RF coupling from an external transmitter, either during actual use by the sleeping patient or during recharging periods in the awake patient.

The microstimulator used with the invention has the following important properties:

(1) A narrow, elongated form factor suitable for implantation through the lumen of a hypodermic needle or laparoscopic instrument;

(2) Electronic components encapsulated in a hermetic package made from a biocompatible material;

(3) At least two electrodes on the outside of the package for the application of stimulation current to surrounding tissue;

(4) An electrical coil inside the package that receives power and data by inductive coupling to a transmitting coil placed outside the body, avoiding the need for electrical leads to connect devices to a central implanted or external controller; and (5) Means for temporary storage of electrical power within the microstimulator.

An implantable microstimulator having the above properties is also known as a BION™ stimulator. The BION stimulator is fully described in other documents, referenced below.

Two main embodiments of the invention are contemplated, one closed loop, and one open loop.

In the closed loop embodiment, the microstimulator devices also provide a sensing function that can be used to trigger the desired stimulation whenever airway obstruction is detected.

In the open loop embodiment, one or more channels of electrical stimulation are applied to nerves or muscles that control the oropharyngeal airway and are then activated in a regular pattern whose period corresponds approximately to the natural respiratory rhythm of the patient. In this open loop embodiment, electrical stimulation is thus applied via the BION stimulator(s) in an open-loop manner, without the complication of additional sensors and other circuits, as are commonly used in a closed loop system. Applied stimulation in such open-loop fashion advantageously entrains the natural biological oscillator associated with the patient's respiration rate, thereby allowing the desired opening of the airwaves to occur during inspiration by the patient.

Further, in accordance with another aspect of the open loop embodiment, the natural frequency of respiration of the patient is determined by observing the patient during sleep, preferably in a posture that minimizes airway obstruction. Such is determined, e.g., by visual observation and a stopwatch, or it can be automated by any of several technologies for monitoring respiration, such as length gauge monitoring of chest expansion, airflow monitoring through a face mask, thoracic electrical impedance, and the like. One or more channels of microstimulators, or BION stimulators, are then "implanted" in the patient. The individual devices are injected into the desired muscles after verifying the correct location of the insertion needle by electrical stimulation of a removable trochar within the hollow sheath of the needle. Ultrasonic imaging of the needle, implants and oropharyngeal structures may also be used during the implantation procedure. After allowing time for the implanted stimulators to stabilize, they are powered up and tested with a range of stimulation parameters (pulse width, current and frequency) to determine the stimulation program that will open the airway. This program is then loaded into a portable controller, which is positioned to control the microstimulators; or, for some embodiments of the microstimulators, may be loaded directly into the microstimulators.

It is thus an object of the present invention to provide a minimally invasive electrical stimulation system for treatment of obstructive sleep apnea (OSA).

It is an additional object of the invention to provide a method of treating sleep apnea through the use of at least one small, implantable microstimulator.

It is another object of the invention to provide a system and method of treating sleep apnea using at least one tiny microstimulator that is minimally invasive to the patient, and which, when the microstimulator(s) is implanted, may be used in either an open loop or closed loop manner, and which is readily adaptable (programmable and/or controllable) to suit the diverse and individual needs of the patient.

It is a further object of the invention to provide a system and method for the treatment of OSA that when used in an open loop manner provides electrical stimulation in a regular pattern whose period corresponds approximately to the natural respiratory rhythm of the patient, and thereby entrains the natural respiratory rhythm of the patient to track that of the applied stimulation.

BRIEF DESCRIPTION OF THE DRAWINGS

The above and other aspects, features and advantages of the present invention will be more apparent from the following more particular description thereof, presented in conjunction with the following drawings and Appendices wherein.

Corresponding reference characters indicate corresponding components throughout the several views of the drawings.

DETAILED DESCRIPTION OF THE INVENTION

Figure 1:
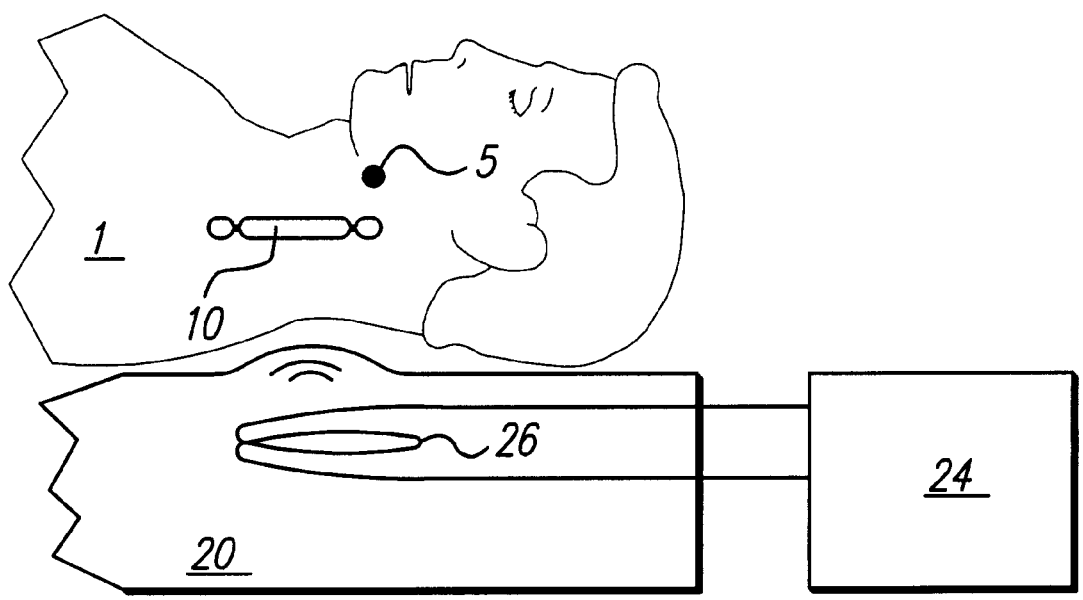
FIG. 1 illustrates one way in which a microstimulator may be used to treat sleep apnea in accordance with the invention.

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention is directed to a method for treating sleep apnea, and more particularly obstructive sleep apnea (OSA) using one or more small implantable microstimulators, also referred to as BION™ devices. Various features and details associated with the manufacture, operation and use of such implantable microstimulators, or BION devices, may be found in one or more of the following documents, all of which are incorporated herein by reference: U.S. Pat. No. 5,193,539, entitled "Implantable Microstimulator"; U.S. Pat. No. 5,193,540, entitled "Structure and Method of Manufacture of an Implantable Microstimulator"; U.S. Pat. No. 5,312,439, entitled "Implantable Device Having an Electrolytic Storage Electrode"; PCT Publication WO 98/37926, published Sep. 3, 1998, entitled "Battery-Powered Patient Implantable Device"; PCT Publication WO 98/43700, published Oct. 8, 1998, entitled "System of Implantable Devices For Monitoring and/or Affecting Body Parameters"; PCT Publication WO 98/43701, published Oct. 8, 1998, entitled "System of Implantable Devices For Monitoring and/or Affecting Body Parameters"; U.S. patent application Ser. No. 09/077,662, filed May 29, 1998, entitled "Improved Implantable Microstimulator and Systems Employing Same"; and Cameron, et al., "Micromodular Implants to Provide Electrical Stimulation of Paralyzed Muscles and Limbs", *IEEE Transactions on Biomedical Engineering*, Vol. 44, No. 9 (September 1997), pages 781–790.

As described in the referenced documents, the microstimulator or BION™ device is a very versatile device that may be used for many applications. Advantageously, such device has a form factor that allows it to be readily implanted through the lumen of a hypodermic needle or laparoscopic instrument, thereby allowing its implantation to occur in a non-invasive manner. (For purposes of this application, "non-invasive" or "noninvasively" is defined to mean without making surgical incisions at the surface tissue of the patient, i.e., no more invasive than the insertion of a hypodermic needle.) Typically, the microstimulator is housed within a tubular housing having a diameter no greater than about 3–4 mm, preferably only about 1.5 mm, and a length no greater than about 10–12 mm. One way to characterize the microstimulator housing is by form factor. As used herein, the term "form factor" is defined as the ratio of the diameter of the housing to its length. The form factor of a preferred microstimulator is 0.4 or less.

Like all newly developed devices, the BION™ device has undergone (and is currently undergoing) various stages of development. At present, there are three levels of BION technology, any one of which may be used to treat obstructive sleep apnea in accordance with the invention. These three levels of BION technology are referred to herein as BION-1 devices, BION-2 devices, and BION-3 devices. A summary of each type of device is provided below.

The BION-1 device provides on-line, inward transmission of power and stimulus command data. The BION-1 system has been built and tested extensively in animals and clinical trials will begin shortly in other applications. It is described in detail in the documents referenced above. The external coil transmits a continuous RF field with amplitude modulation to encode digital data. Each implant receives the RF energy, converts it into a regulated DC supply to operate its integrated circuit chip, and stores stimulus pulse energy in a capacitor (either discrete capacitor in the hermetic package or an electrolytic capacitor formed by the stimulating electrodes themselves and the saline body fluids). When the implant receives the appropriate command data, it generates the required stimulation pulse releasing energy stored in the capacitor, and then recharging the capacitor between output pulses.

The BION-2 device provides on-line, inward power transmission plus bidirectional data transmission supporting sensing and telemetry functions. The BION-2 devices utilize a new scheme for data transmission called "suspended carrier transmission". Suspended carrier transmission is about ten times more efficient than the transmission scheme utilized with BION-1 devices (thereby making it possible for BION devices to be powered by battery-operated controllers) and it permits the power transmission carrier to be switched off for brief periods so that the implants can sense low level signals and telemeter out data on the same carrier frequency without being overwhelmed by the strong power carrier signal. Suspended carrier transmission is described in U.S. Pat. No. 5,697,076, incorporated herein by reference.

Advantageously, one potentially important function of the BION-2 (and BION-3) devices is the ability of one BION implant device to monitor the outgoing data transmission from another BION implant device. This can be used to relay sensing and command signals between implants and to monitor the relative distance and orientation between two implants in order to measure mechanical motion of the tissues in which the BION devices are implanted. For example, the attempt to suck air through an obstructed airway is likely to be accompanied by various deformations of the normal size and position of airway structures such as the trachea and larynx, which deformations may be sensed by continuously monitoring the relative position between one BION device attached to the moveable structure and another BION device attached to an adjacent reference structure. One such deformation is retraction, in which the obstructed larynx and trachea are stretched downward by the inspiratory effort of the diaphragm.

Another approach that may be used with the BION-2 devices to facilitate sensing various parameters is to detect the electromyographic signals in accessory respiratory muscles of the neck and/or chest. These muscles are normally relatively quiescent during unobstructed respiration, but become active when additional inspiratory effort is applied as the sleeping patient tries to overcome the obstruction. Both the BION-2 device and BION-3 device are being designed to detect such low level bioelectric signals. While the detection of electromyographic signals is complicated somewhat by activation of these accessory respiratory muscles during turning and other postural shifts, such complications are overcome by additional sensing of acceleration of BION implant devices, another capability included within selected versions of BION devices.

The BION-3 device includes bidirectional data telemetry plus a rechargeable battery (or other power storage component, such as an ultracapacitor) permitting autonomous function in the absence of external power transmission. Preferably, each BION 3 device is powered by a miniature rechargeable battery (e.g., lithium ion technology) within its hermetic package, as described in some of the above-referenced documents. The internal battery is capable of sustaining internal clocking and logic and output pulses for a period of hours to days (depending on stimulus parameters). The internal battery, or other power source, is recharged during relatively brief periods of time, e.g., 10–30 minutes, when the BION implant devices receive power from an external coil. Stimulation parameters and other control functions are updated by data transmission from the external controller at this time. A simple means for manually starting and stopping preprogrammed operation is also provided, such as a portable magnet or RF transmitter that may be worn by the patient.

Turning next to the figures, the method of using BION™ devices for treating obstructive sleep apnea in accordance with the various embodiments of the invention will be described. Many different combinations of devices and functions are possible for stimulation, power, sensing and control. The following descriptions are intended to be illustrative only of the various ways a microstimulator may be used to treat sleep apnea, and are not intended to be limiting. It should also be noted that the accompanying drawings are not drawn to scale. In actuality, the BION devices are very tiny, about the size of a large grain of rice.

As seen in FIG. 1, for example, one or more BION implant devices 10 receive power and command signals from a transmission coil 26 placed under the patient 1. The transmission coil, for example, may be placed in the pillow or mattress cover 20. An external bedside controller 24 that is powered from conventional power lines sends a preprogrammed sequence of stimulation commands to the implant device(s) 10, causing them to stimulate motor and/or sensory nerves at target sites 5. This electrical stimulation, in turn, results in direct or reflexive muscular contraction that opens the airway continuously or at regular intervals during sleep.

Figure 2:
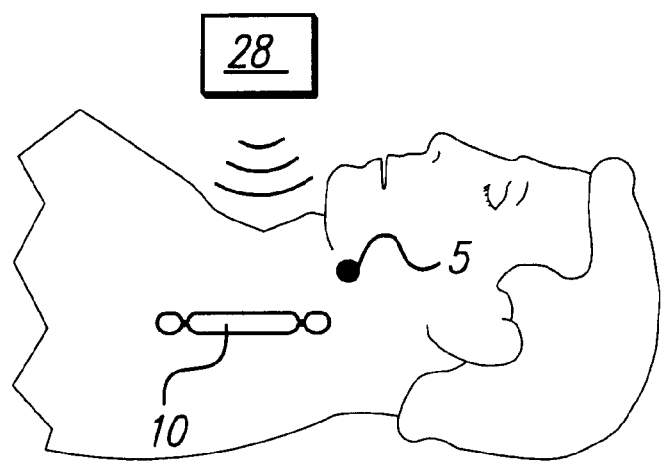
FIGS. 2 and 3 respectively illustrate ways in which control and/or energy signals may be sent to control and/or energy-storage elements within an implantable microstimulator during sleep (FIG. 2) and during non-sleep (FIG. 3) conditions.
Figure 3:
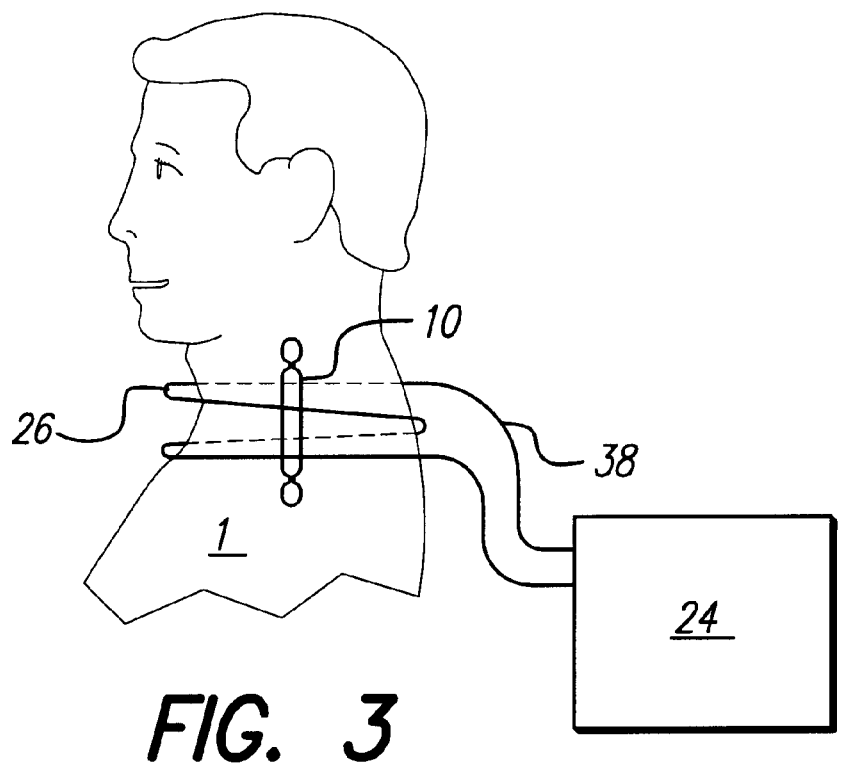

In one embodiment, as seen, e.g., in FIGS. 1, 2 or 3, one or more BION 3 implant devices 10 use energy stored in their rechargeable batteries to stimulate motor and/or sensory nerves at target sites 5, resulting in direct or reflexive muscular contraction that opens the airway continuously or at regular intervals during sleep. The batteries in the BION 3 implant devices 10 are recharged as required by donning a transmission coil 26 that is connected to a controller 24 that receives its power from conventional power lines. The controller 24 transmits data specifying the stimulation parameters to reassert or modify the stimulation pulses that will be generated when the BION-3 implants are operating. As needed, the patient 1 can turn the BION-3 implants on or off by operating a portable remote control device 28.

Figure 4:
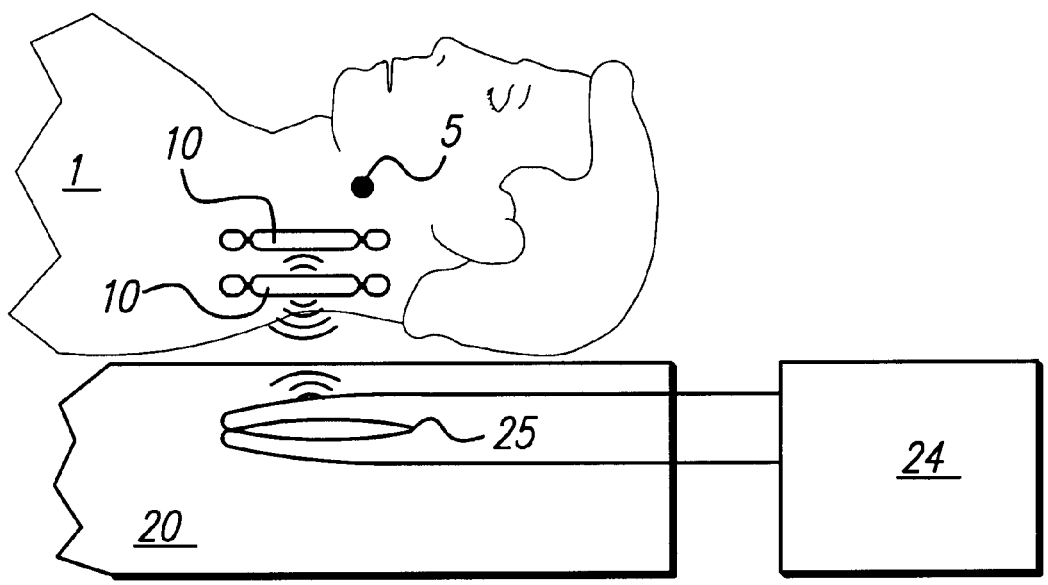
FIG. 4 illustrates the use of at least two BION devices and an external controller/recharging unit.

In another embodiment, a closed loop embodiment, one or more BION-2 implant devices 10 are implanted in the patient 1, as illustrated in FIG. 4, with at least one such BION-2 implant device acting as a sensor of airway occlusion. The sensing function is realized, e.g., utilizing airway pressure, characteristic snoring sounds, mechanical motion, muscle activity or other means for detecting occlusion. Information from the sensing function is transmitted from the sensing BION device to an external bedside controller 24, which utilizes such information to decide when and what stimulation is required to alleviate the occlusion, according to prescribing information stored in the bedside controller 24 by the clinician. The bedside controller 24 transmits stimulation commands to one or more of the BION-2 implant devices. Data transmission in both directions is conveyed via a transmission coil 26 placed under the sleeping patient, for example in the pillow or mattress cover 20.

In still a further embodiment, also represented by the configuration shown in FIG.4, one or more BION-3 implant devices 10 perform both sensing and stimulus functions according to control information stored within the BION-3 implant devices. Power to recharge the batteries included as part of the BION-3 devices 10, as well as control signals to operate the BION-3 device according to a prescribed operating program, are transmitted to the BION-3 implants during occasional recharging periods, using a suitable external recharging/programming unit 24, at which time the patient dons a transmission coil 26, as shown in FIG. 3, or lies adjacent a transmission coil 26, as shown in FIG. 4, that is connected to a controller 24. The controller 24 receives its power from conventional power lines or from a removable, replaceable battery.

Figure 5:
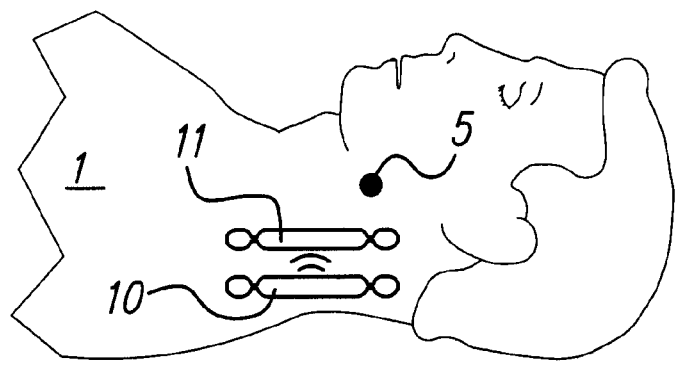
FIG. 5 illustrates the use of two BION devices used in a closed-loop system to treat sleep apnea, one having a built-in sensor that is able to sense a blocked airway and communicate such sensed data to the other BION device, which other BION device then initiates a stimulation sequence aimed at unblocking the airway passage.

In yet another embodiment, illustrated in FIG. 5, at least one BION implant device 10 functions as a transmitter and transmits sensor data concerning airway occlusion to at least one other BION implant device 11. The device 11 thus functions as a receiver and uses the received data to initiate a stimulation sequence that has been previously stored in the BION device 11.

Figure 6:
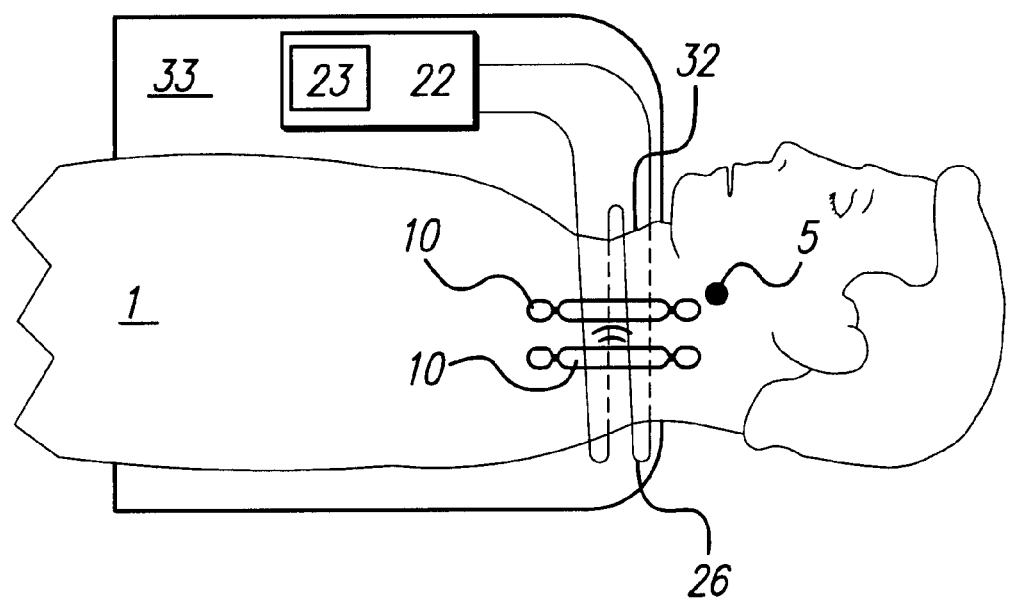
FIG. 6 illustrates an alternate method of coupling the external controller/recharging unit with the implanted microstimulator devices.

With reference to FIG. 6, it is noted that when power and data transmission are conveyed via a transmission coil 26 worn on the patient, such coil 26 may be included as part of a collar around the neck 32, a vest 33, or other suitably located garment. Alternatively, the coil 26 may be contained within an adhesive patch that can be affixed to the skin in the vicinity of the BION implant device(s).

The transmission coil 26 may be controlled and powered by electronic circuitry 22 containing batteries 23 for power, as seen in FIG. 6. Such circuitry 22 may also be worn on the patient; as shown in FIG. 6, or such circuitry may be controlled and powered via an electrical cable 38 that tethers the patient to a bedside controller 24, as seen in FIG. 3. The bedside controller, in turn, receives its operating power from conventional power lines or from replaceable batteries.

Figure 7:
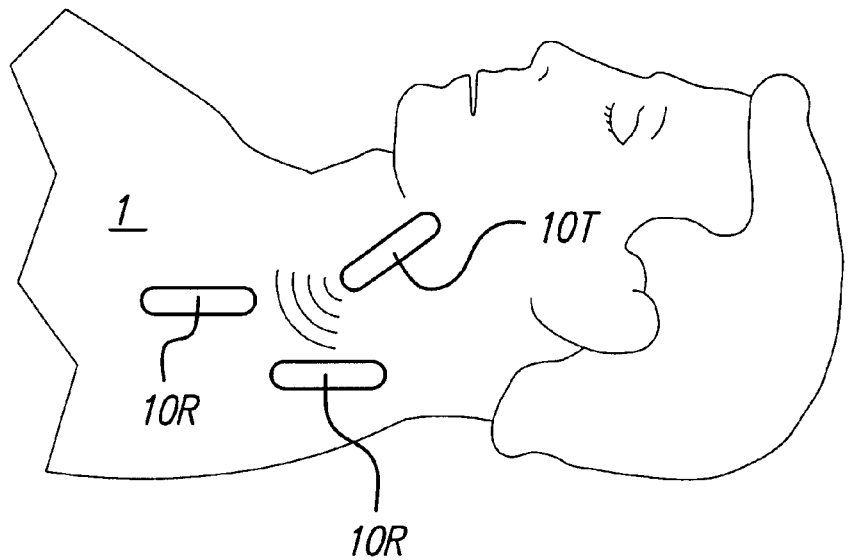
FIG. 7 illustrates a multichannel stimulation system using battery-powered microstimulators.

Advantageously, an implanted battery-powered microstimulator, e.g., a BION-3 device, may be programmed to self-generate the desired stimulation pattern at a desired rate. If more than one channel of stimulation is desired, it is necessary to have more than one battery-powered microstimulator implanted, as well as a means to synchronize the operation of the various autonomous implants. This may be done as illustrated in FIG. 7. As seen in FIG. 7, at least one microstimulator 10T functions as a transmitter, emitting energy that the other microstimulators 10R can receive and detect. In one embodiment, the energy emitted by the microstimulator 10T is in the form of the stimulation pulse itself produced by the transmitting microstimulator 10T, which is detected as a stimulus artefact on the electrodes of receiving microstimulators 10R. Alternatively, the energy emitted by the microstimulator 10T may be a pulse of radio frequency energy detected by mutual inductance between the coils contained within each receiving microstimulator 10R.

The transmitting microstimulator 10T is programmed to stimulate the tissue in which it is located and to transmit to the other implant microstimulator devices at the desired respiratory rate. The receiving microstimulators 10R are programmed to generate stimuli if and only if they detect the energy emitted by transmitting microstimulator 10T. For BION-3 devices, i.e., battery-powered microstimulators 10, means are also provided to start and stop the autonomous function, to download revised stimulation parameters, and to recharge the batteries at regular intervals. All of these functions may be accomplished by inward RF power and telemetry links as depicted in FIGS. 1, 2, 5 and 6.

In order to use the microstimulator in an open loop system wherein electrical stimuli are applied to open the blocked airway passage at a rate that approximates the patient's natural respiratory rate, it is first necessary to determine that patient's natural respiratory rate, and then determine if such natural rate can be entrained to follow the rate of the applied stimuli. This may be accomplished as illustrated in FIG. 8.

Figure 8:
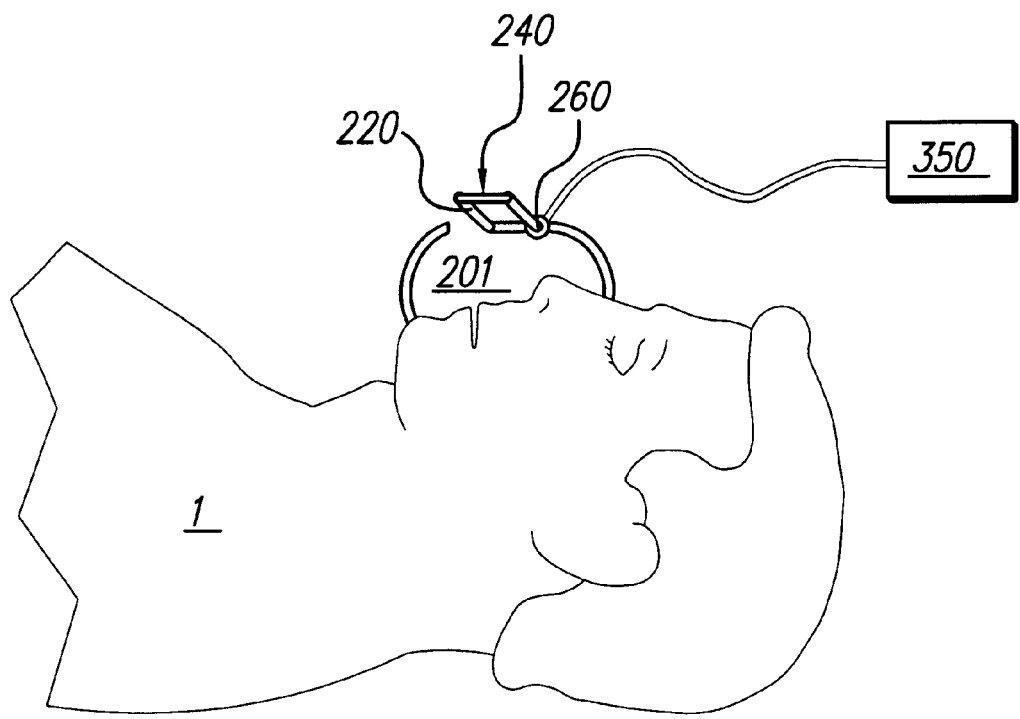
FIG. 8 depicts one manner in which the invention may be tested using a special type of face mask.

As shown in FIG. 8, the patient 1, while in a lying or sleeping position, is fitted with a face mask 201. The face mask 201 is equipped with a flap valve 220 coupled by mechanical means 240 to an electromechanical actuator 260, such as a solenoid or motor. In its passive state, the flap valve 220 simulates OSA by occluding the inlet passage to the mask on inspiration only. Activation of the electromechanical actuator 260 simulates regular periods of oropharyngeal muscle stimulation by holding the passage open at the desired intervals. The subject falls asleep with the flap valve 220 held open; then the open/closed cycling is applied by controller 350 to see if the subject is able to breath adequately.

One important observation obtained from using a system like that illustrated in FIG. 8 is the pattern of respiration that ensues when the valve 220 happens to be closed at the time of an inspiration, mimicking the typical airway obstruction. This occurs in a system using microstimulator implants, as described, e.g., above in connection with FIGS. 1–6, following a prolonged respiratory interval such as a sigh or a phase shift of the normal rhythm, e.g., as occurs during a postural shift. When this prolonged respiratory interval occurs, the occluded inspiratory phase is prolonged so that it persists until the valve 220 is opened electronically, or the subsequent inspiratory phases will be gradually phase-shifted so that they coincide with a valve-open period within a couple of cycles.

The entraining technique shown in FIG. 8 is a simple, noninvasive procedure that may easily be carried out in a conventional sleep disorders diagnostic laboratory. The mask 201 is readily made by those of skill in the art of biomedical engineering. Until sufficient data is developed to show otherwise, and because patients may likely differ in their patterns of response to an occlusion occasioned by wearing the mask, extensive individual testing of prospective patients for receipt of the implanted microstimulators 10 is highly recommended.

As described herein, it is thus seen that the invention provides a method of treating sleep apnea through the use of at least one small, implantable microstimulator. Such method includes implanting at least one BION implant device near a target site containing muscle and/or nerve tissue, and thereafter controlling the at least one BION implant device to apply electrical stimuli to the muscle and/or nerve tissue in accordance with a prescribed stimulation regime, which stimulation regime is aimed at opening up the blocked airway. For example, a burst of n stimulation pulses, where n is an integer of e.g., 2 to 20, or more, may be applied to muscle tissue near the blocked airway upon sensing a blockage. Alternatively, a burst of n stimulation pulses may be regularly applied to a patient having a history of blocked airways on a regular basis, while the patient is sleeping. Or, a single stimulation pulse may be applied to targeted tissue of the sleeping patient on a regular basis, or when a blockage is sensed. Indeed, many different types of stimulation sequences may be applied to appropriate tissue and/or nerves in order to achieve the objectives of the invention (i.e., to cause a muscle contraction that opens a blocked airway).

As further described herein, it is seen that the invention provides a system and method of treating sleep apnea that is minimally invasive to the patient, and which, once implanted, is readily adaptable (programmable and/or controllable) to suit the diverse and individual needs of the patient. In one embodiment, the implantable microstimulators are used in an open loop manner and assist in entraining the respiratory rate of the patient to match the programmed rate of the microstimulator(s). In another embodiment, the implantable microstimulators are used in conjunction with one or more sensors in a closed loop manner, and assist in stimulating target tissue at an appropriate time in the respiratory cycle.

While the invention herein disclosed has been described by means of specific embodiments and applications thereof, numerous modifications and variations could be made thereto by those skilled in the art without departing from the scope of the invention set forth in the claims.

What is claimed is:

1. A method of treating obstructive sleep apnea (OSA) using an electrical stimulator controllable to provide electrical stimulation pulses in accordance with a regular stimulation pattern having a controlled rhythm comprising:
   (a) determining an approximate natural respiration cycle of a patient;
   (b) positioning electrodes in or on the patient at a location near the oropharynx muscles; and
   (c) applying an electrical stimulus to the electrodes from the electrical stimulator at a rate that approximates the rate of a natural respiration cycle, wherein the oropharynx muscles are stimulated to pull open obstructed airways at a rhythm that is the same as or close to the natural respiration cycle;
   wherein the respiratory rate of the patient is entrained to follow the rhythm of the electrical stimulator, whereby obstructed airways are kept open; and
   wherein the electrodes comprise part of an injectable microstimulator.

2. The method of claim 1 wherein the positioning of the electrodes in or on the patient at a location near the oropharynx muscles comprises injecting the microstimulator so that the microstimulator is positioned near the oropharynx muscles.

3. The method of claim 2 wherein the step of applying an electrical stimulus to the electrodes comprises controlling the injectable microstimulators so that they provide a stimulus at a rate that approximates the natural respiration rate.

4. The method of claim 1 wherein determining the patient's natural respiration rate comprises using a diagnostic face mask that simulates obstruction and opening of the patient's airway at a controlled rate.

5. A method of treating obstructive sleep apnea (OSA) using an electrical stimulator controllable to provide electrical stimulation pulses in accordance with a regular stimulation pattern having a controlled rhythm comprising:

(a) determining an approximate natural respiration cycle of a subject;

(b) positioning electrodes near the oropharynx muscles of the subject; and (c) applying an electrical stimulus to the electrodes to pull open obstructed airways at a rhythm that is the same as or close to the natural respiration cycle;

wherein the electrodes comprise part of an injectable microstimulator.

6. The method of claim 5 further comprising adjusting a rate of the applied stimulus so as to entrain the respiration cycle of the subject to follow the applied stimulus rate.

7. The method of claim 5 wherein positioning the electrodes near the oropharynx muscles comprises injecting the microstimulator so that the microstimulator is positioned near the oropharynx muscles.

8. The method of claim 6 wherein determining an approximate natural respiration cycle of the subject comprises using a diagnostic face mask that simulates obstruction and opening of the subject's airway at a controlled rate.

* * * * *